United States Patent [19]

Ninagawa et al.

[11] Patent Number: 4,593,145
[45] Date of Patent: Jun. 3, 1986

[54] PROCESS FOR PRODUCING ISOPRENE

[75] Inventors: Yoichi Ninagawa, Matsudo; Osamu Yamada; Tsumoru Renge, both of Hasaki; Sunao Kyo, Abiko; Takayoshi Osaki, Kurashiki; Koichi Kushida, Ibaraki, all of Japan

[73] Assignee: Kuraray Company Limited, Kurashiki, Japan

[21] Appl. No.: 707,842

[22] Filed: Mar. 4, 1985

Related U.S. Application Data

[63] Continuation-in-part of Ser. No. 540,870, Oct. 11, 1983.

[30] Foreign Application Priority Data

Oct. 14, 1982 [JP] Japan ............................ 57-180759

[51] Int. Cl.$^4$ .............................................. C07C 1/20
[52] U.S. Cl. ...................................... 585/607; 585/608
[58] Field of Search .................................. 585/607, 608

[56] References Cited

U.S. PATENT DOCUMENTS

| | | | |
|---|---|---|---|
| 2,350,485 | 6/1944 | Arundale et al. | 585/608 |
| 3,890,404 | 6/1975 | Takagi et al. | 585/608 |
| 4,067,923 | 1/1978 | Belyren et al. | 585/608 |

*Primary Examiner*—Curtis R. Davis
*Attorney, Agent, or Firm*—Oblon, Fisher, Spivak, McClelland & Maier

[57] ABSTRACT

A process for producing isoprene in good yield is provided. The process is characterized in that an alkyl tertiary butyl ether and a formaldehyde source are fed, together with water, into a acidic aqueous solution continuously or intermittently while maintaining the reaction pressure in an adequate range and at the same time distilling off the product isoprene, unreacted starting materials, isobutene and tertiary butanol, together with water, from the reaction zone.

16 Claims, 1 Drawing Figure

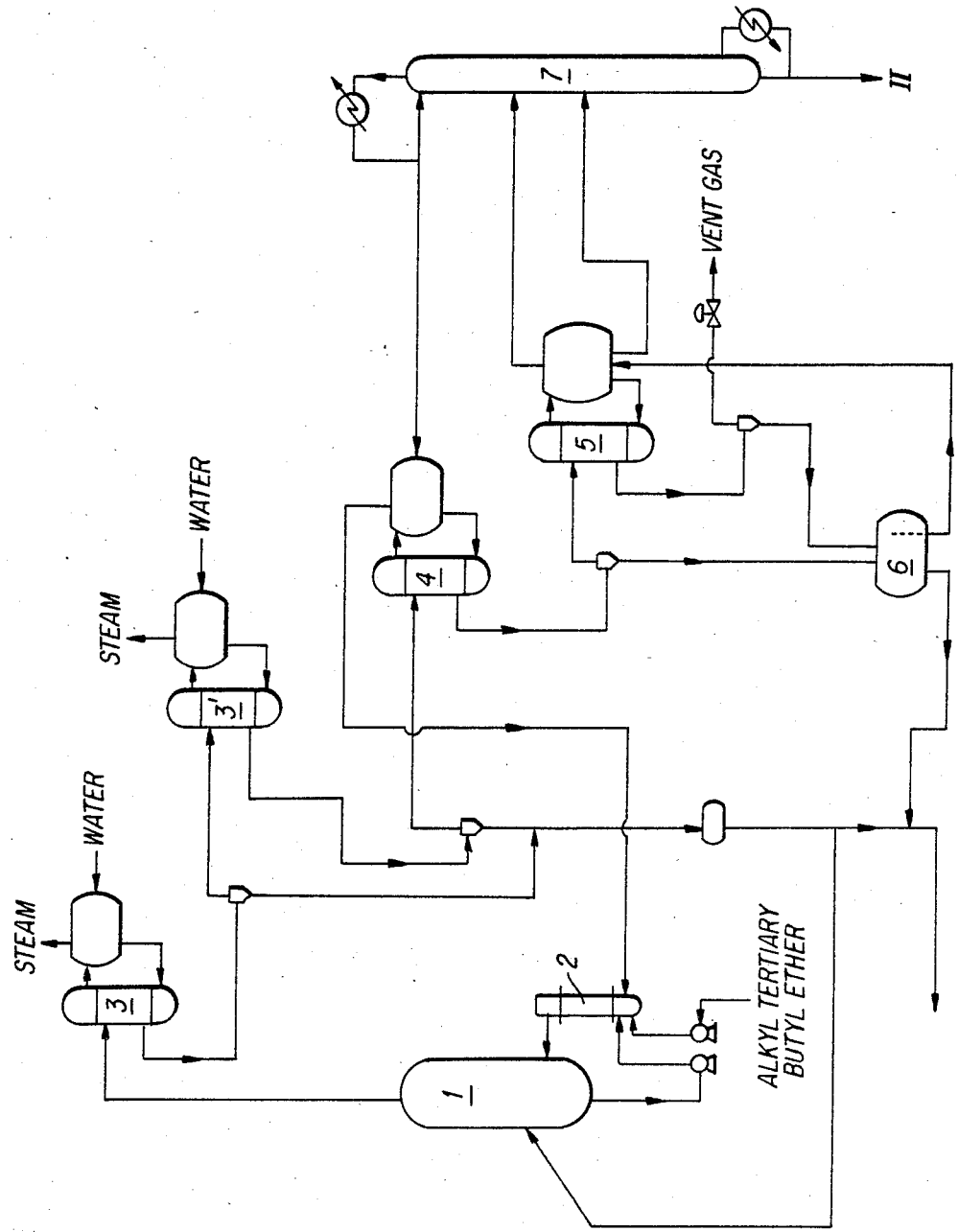

PROCESS FOR PRODUCING ISOPRENE

CROSS REFERENCE TO RELATED APPLICATION

This application is a continuation-in-part of our earlier copending application, Ser. No. 540,870, filed Oct. 11, 1983.

BACKGROUND OF THE INVENTION

1. Field of the Invention

This invention relates to a process for producing isoprene by reacting an alkyl tertiary butyl ether with formaldehyde.

2. Description of the Prior Art

Attempts to synthesize isoprene in one step by reacting isobutene or its precursor such as tertiary butanol or an alkyl tertiary butyl ether with formaldehyde have been made repeatedly and a number of processes have been proposed.

For instance, Japanese Kokai Tokkyo Koho (laid-open patent application) No. 46-6,963 discloses a gaseous phase process using a phosphoric acid-calcium oxide-chromium oxide catalyst. However, this process is far from practicable because the catalyst life is short.

Liquid phase processes using various aqueous acid solutions as the catalysts are disclosed in U.S. Pat. No. 3,890,404, Japanese Patent Publication No. 52-30,483 and Japanese Kokai Tokkyo Koho Nos.57-130,928 and 58-69,824. In U.S. Pat. No. 3,890,404, for instance, it is indicated that when the reaction was conducted at 160° C. for 18 minutes using $FeCl_2$ as the catalyst, isoprene was formed in a yield of 82% of the formaldehyde basis (Example 32). However, in check experiments performed by the present inventors, the procedures described in Example 32 of U.S. Pat. No. 3,890,404, Example 2 of Japanese Patent Publication No. 52-30,483 and Example 8 of Japanese Kokai Tokkyo Koho No. 57-130,928 gave isoprene yields of about 50% or below, as shown later in Reference Examples. Other examples than the above, when checked, gave nothing but similarly low isoprene yields.

U.S. Pat. No. 4,067,923 discloses that isoprene was formed in an yield exceeding 70% when the reaction was carried out batchwise or in the manner of a piston flow using a sulfanilic acid as the catalyst. However, check experiments by the present inventors revealed that the main product was 4,4-dimethyl-1,3-dioxane and that isoprene was formed in a very small amount (refer to Reference Example 5 to be mentioned later). According to the above cited reference, the reaction is carried out in a closed system at a temperature not lower than the critical point of isobutene. However, such reaction conditions require a high pressure, hence a large cost of equipment.

Furthermore, U.S. Pat. No. 2,350,485 describes various reaction modes for producing conjugated diene by the reaction of a tertiary olefin, a tertiary alcohol or a tertiary halides and an aldehyde. However, the disclosure contains only one example which is concerned with the reaction of 2-methyl-2-butene with formaldehyde in a closed system, and, according to said example, the yield of 2,3-dimethyl-1,3-butadiene is as low as 23%. When the present inventors reacted isobutene with formaldehyde under the same conditions as in said example, the yield of isoprene was similar to that of 2,3-dimethyl-1,3-butadiene just mentioned above.

As mentioned hereinabove, the one-step production of isoprene from isobutene and/or its precursor such as a tertiary butanol or an alkyl tertiary butyl ether and formaldehyde involves various problems to be solved. This is one of the major reasons why the so-called two-step process which involves the production of 4,4-dimethyl-1,3-dioxane as an intermediate has been employed for the commercial production of isoprene.

SUMMARY OF THE INVENTION

Intensive research by the present inventors in order to solve these prior art technological problems encountered in the one-step liquid-phase process for producing isoprene using an alkyl tertiary butyl ether and formaldehyde sources as low materials has now led to the present invention. According to the invention, isoprene can be produced in good yield by reacting an alkyl tertiary butyl ether with formaldehyde in an acidic aqueous solution under the following conditions:

(a) that the acidic aqueous solution is present in the reaction zone, (b) that said alkyl tertiary butyl ether, a formaldehyde source and water are fed to said reaction zone continuously or intermittently, and (c) that isoprene, water, unreacted starting materials, isobutene, tertiary butanol and other low-boiling components are distilled off from said reaction zone, the amounts of said alkyl tertiary butyl ether and formaldehyde source being fed to said reaction zone being such that the alkyl tertiary butyl ether-to-formaldehyde molar ratio in the charge is at least 2 and the pressure in the reaction system being maintained at a level 1.2 to 3.5 times the vapor pressure at the reaction temperature of the acidic aqueous solution existing in the reaction zone, said alkyl tertiary butyl ether-to-formaldehyde molar ratio being calculated by calculating the amount of the formaldehyde source in formaldehyde equivalent when said source is other than formaldehyde. Under the reaction conditions, the alkyl tertiary butyl ether is converted partially into isobutene and tertiary butanol, and a part of isobutene reacts with formaldehyde to give isoprene. The vapor pressure at the reaction temperature of the acidic aqueous solution is a physical constant definitely determined depending on the kind and concentration of the acidic substance containing in said acidic aqueous solution.

In accordance with another aspect of the present invention, isoprene can be produced in more improved yield by conducting the reaction in the manner characterized in:

(a) that the acidic aqueous solution is present in plural reaction zones connected in series, (b) that an alkyl tertiary butyl ether is fed to the first reaction zone continuously or intermittently while a formaldehyde source and water are fed to each reaction zone continuously or intermittently, (c) that isoprene, water, unreacted starting materials, isobutene, tertiary butanol and other-boiling components are distilled off from each reaction zone except the last one and fed to the subsequent reaction zone, and (d) the isoprene, water, unreacted starting materials, isobutene, tertiary butanol and other low-boiling components are distilled off from the last reaction zone, the amounts of said alkyl tertiary butyl ether and formaldehyde source being fed to the first reaction zone being such that the alkyl tertiary butyl ether-to-formaldehyde molar ratio in the charge is at least 2, the amounts of said alkyl tertiary butyl ether, isobutene and/or tertiary butanol (i.e. isobutene source) and formaldehyde source being fed to each reaction zone exclusive of the first reaction zone being such that the said isobutene source-to-formaldehyde molar ratio in the charge is at least 2, and the pressure in the reaction system being maintained at a level 1.2 to 3.5 times the vapor pressure at the reaction temperature of the acidic aqueous solution existing in the reaction zone, said isobutene source to-formadehyde molar ratio being calculated by calculating the amount of the formaldehyde source in formaldehyde eqivalent when said source is other than formaldehyde.

The process according to the invention have many advantages. For instance, the process is good in workability and stability during working, the catalyst life is long, the reaction can be conducted at a relatively low temperature and under a relatively low pressure, and therefore the cost of equipment can be reduced.

When the desired product is more volatile than the reactants, the yield of the product can generally be increased very effectively by conducting the reaction while distilling off said product. In this case, the concentration of the reactants in the liquid existing in the reaction zone becomes higher and the concentration of the product lower as compared with the distillate, so that side reactions are inhibited and as a result the yield increases. A typical example can be seen in the production of isoprene by dehydration of 3-methyl-1,3-butanediol (refer to Japanese Kokai Tokkyo Koho No. 54-163,504).

On the other hand, when using reactants more volatile than the product, the reaction is performed while distilling off the product, an improved yield can hardly be expected but the yield generally tends to decrease because the concentration of the reactants in the liquid existing in the reaction zone becomes lower and the concentration of the product higher as compared with the distillate. For the reaction of the alkyl tertiary butyl ether and formaldehyde, first the alkyl tertiary butyl ether is converted partially into isobutene and a part of isobutene reacts with formaldehyde to give isoprene so that the mode of reaction with simultaneous distillation seems disadvangeous, since the alkyl tertiary butyl ether is much more volatile than the product, namely isoprene. This is presumably the reason why, amoung many reports so far made concerning the reaction of the alkyl tertiary butyl ether and formaldehyde, none mentioned an embodiment of such reaction-with-distillation process. The above-cited U.S. Pat. No. 2,350,485 refers to, as one of the modes of reaction, the mode of conducting the reaction while distilling off the products and reactants but does not mention any specific reaction conditions at all. There is not found any mention of the influence on the yield as exerted by this mode of the reaction to be conducted while distilling off the product and reactants. The present inventors conducted the reaction of an alkyl tertiary butyl ether with formaldehyde in an acidic aqueous solution with simultaneous distillation and found that isoprene can be formed in high yields, which could not be attained by the reaction in a closed system, by maintaining, as mentioned above, the pressure within the reaction system and the alkyl tertiary butyl ether-to-formaldehyde molar ratio or the isobutene source-to-formaldehyde molar ratio each within an adequate range.

DETAILED DESCRIPTION OF THE INVENTION

In the following description, the alkyl tertiary butyl ether is sometimes referred to as "ATBE" and the formaldehyde source as "FA". Furthermore, the number of moles the isobutene source is sometimes referred to as "C", the number of moles of formaldehyde as "F", the molar ratio of the isobutene source to the formaldehyde as "C/F", and the vapor pressure at the reaction temperature of the acidic aqueous solution as "Pw".

The basic process according to the invention consists in that ATBE, FA and water are fed into an acidic aqueous solution continuously or intermittently while distilling off isoprene together with water, unreacted starting materials, isobutene, tertiary butanol and other low-boiling components from the reaction system and that, while carrying out the reaction in the above manner, the ratio C/F (in this case, it means a molar ratio between ATBE and FA to be fed to the reaction zone) and the pressure of the reaction system are maintained within an adequate range respectively. Said "other low-boiling components" include substances which are distilled off from the reaction zone together with water under the reaction conditions, for instance, volatile byproducts.

In carrying out the reaction according to the process of the invention, the ratio C/F (in the case of a single or first reaction zone, it means a molar ratio between ATBE and FA to be fed to the reaction zone) is required to be at least 2. When said ratio C/F is smaller than 2, the yield of isoprene will drop. From the viewpoint of selectivity, a greater C/F ratio is more preferred, hence, in a strict sense, there is no upper limit thereto. However, excessively large C/F ratios does not always result in efficiently improved isoprene yields. Since the heat consumption increases as the ratio C/F increases, it is generally recommended that the C/F should be not more than 40. The preferred ratio C/F is in the range of 3 to 20.

When the reaction mode comprising feeding ATBE, FA and water, optionally together with a low-boiling component which is inert under the reaction conditions, into an acidic aqueous solution which distilling off isoprene and water, together with isobutene, tertiary butanol and other low-boiling components, from the reaction zone is employed, the proportion between each component evaporable from the reaction zone and water can be controlled by adjusting the pressure of the reaction system. Thus, when the pressure of the reaction system becomes high, the proportion of water to the sum of other components in the distillate becomes decreased, whereas, when the reaction system pressure is low, a converse phenomenon takes place. For merely causing the reaction to proceed, any pressure higher than Pw can be selected as the pressure of the reaction system. However, it has been found that, for producing isoprene in good selectivity and in an economically advantageous manner, the pressure within the reaction system (when a low-boiling compound inert under the reaction conditions is fed, the pressure after subtraction of the partial pressure thereof) is required to be within the range of 1.2 to 3.5 times Pw. When said pressure exceeds $3.5 \times Pw$, the isoprene yield becomes markedly decreased. This tendency is apparently seen in selectivity to isoprene based on ATBE. If the pressure within the reaction system is lower than $1.2 \times Pw$, then the conversion of formaldehyde decreases and, in addition, the proportion of water to isoprene in the distillate increases, leading to an increased consumption of heat energy, although the decrease in isoprene yield is not significant.

Since, as mentioned above, ATBE which is converted partially into isobutene and tertiary butanol under the reaction conditions is used in excess over formaldehyde in carrying out the process according to the invention, most of ATBE fed into acidic aqueous solution in the reaction zone distills off as unreacted ATBE, isobutene and tertiary butanol. This isobutene source distilled off (hereinafter, referred to as "BYIB") can be separated from other components and reused by means of circulation. In the improved process according to the invention, the BYIB can be fed to the second reaction zone or subsequent reaction zones.

The improved process according to the invention consists in that plural reaction zones are connected in series, ATBE is fed to the first reaction zone continuously or intermittently and the distillate from the each reaction zone is fed to the subsequent reaction zone. In the improved process, it is very important that the molar ratio C/F ( in the case of the first reaction zone, it means a molar ratio between ATBE and FA to be fed, and in the case of the reaction zone exclusive of the first reaction zone, it means a molar ratio between BYIB and FA to be fed) is maintained within the range of 2 to 40, preferably, 3 to 20, and the pressure of the reaction system is maintained within the range of 1.2 to 3.5 times Pw, too.

When the reaction is conducted in plural reaction zones, the heat consumption depends on the ratio C/F between the reactants fed throughout all the reaction zones. Therefore, the ratio C/F between the reactants fed throughout all the reaction zones should preferably be not more than 40. In the case, the ratio C/F for each reaction zone is selected within an adequate range such that the overall ratio C/F for all the reaction zones does not exceed 40.

Conditions more favorable to the formation of isoprene can be obtained by using plural reaction zones and thereby increasing the ratio C/F between the reactants to be fed to each reaction zone without varying the total volume of the reaction zones and the ratio C/F between the reactants to be fed throughout all the reaction zones. Moreover, since not only the rate of feeding FA but also the rate of feeding water, the pressure within the reaction system, the reaction temperature, the acidity of the acidic aqueous solution and the volume of the reaction zone can be selected in an adequate manner for each reaction zone, the increase in isoprene yield as caused by increasing the ratio C/F between the reactants to be fed to each reaction zone can exceed the loss of isoprene due to consecutive reactions thereof and, as a result, an increased isoprene yield can be achieved at the same overall C/F ratio as compared with the case in which the reaction is conducted in a single reaction zone. In other words, the ratio C/F between the reactants to be fed throughout all the reaction zones as required for achieving the same isoprene yield can be reduced as compared with the case in which the reaction is performed in a single reaction zone, so that the amount of the isobutene source to be used and the amount of water to be evaporated can be reduced, whereby isoprene can be produced advantageously from the energy viewpoint. For increasing the isoprene yield using plural reaction zones while maintaining the ratio C/F between the reactants to be fed throughout all the reaction zones at a constant value, the number of reaction zones should preferably be greater. However, the yield-increasing effect is maximal when the number of reaction zones is increased from 1 to 2. Said effect decreases as said number is increased from 2 to 3, from 3 to 4, and so on. Generally, the number of reaction zones is selected within the range of 2-4 in view of the ratio C/F between the reactants to be fed to each reaction zone as well as the complexity of reaction operations. While it is preferable to feed the whole amount of ATBE to be subjected to reaction to the first reaction zone, it is also possible to feed part thereof to the second and subsequent reaction zones. Generally, however, this offers no particular advantage. FA, another starting material, is fed dividedly to the reaction zones. The proportions of FA for the respective reaction zones can adequately be decided in view of the amount and acidity of the acidic aqueous solution in each reaction zone.

From the energy viewpoint, the vapor from a reaction zone as it is in the gaseous form is preferably fed to the next reaction zone, although it may be condensed wholly or partly prior to submission to the next reaction zone. For smooth passage of the distillate, a later reaction zone is preferably placed under a lower reaction system pressure. Therefore, for achieving favorable reaction results and smooth progress of the reaction, the amount of water to be fed to each reaction zone is selected in an adequate manner so that a later reaction zone is under a lower reaction system pressure while the pressure of the reaction system maintaining the above relation. The reaction temperature and the acidity of the acidic aqueous solution may be varied according to the respective reaction zones or maintained at constant levels throughout all the reaction zones.

The formaldehyde source to be used in practicing the invention is, for instance, an aqueous formaldehyde solution or gaseous formaldehyde. Trioxane, paraformaldehyde and others which decompose under the reaction conditions to give formaldehyde may also be used. Formals such as methylal are also usable. Since water is fed to the reaction zone and formaldehyde takes the form of aqueous solution in the reaction zone, it is advantageous from the operation viewpoint to use an aqueous formaldehyde solution as the formaldehyde source.

The alkyl tertiary butyl ether to be used in the process according to the present invention has the general formula as shown by $ROC(CH_3)_3$ wherein R is an alkyl group having not more than 5 carbon atoms. Preferred examples of the alkyl tertiary butyl ether are methyl tertiary butyl ether, ethyl tertiary butyl ether, n-propyl tertiary butyl ether, isobutyl tertiary butyl ether, n-amyl tertiary butyl ether, 3-methylbutyl tertiary butyl ether and 2-methylbutyl tertiary butyl ether. Amoung them, methyl tertiary butyl ether is most suitable for the invention. The alkyl tertiary butyl ether may contain other compounds as well as isobutene, tertiary butanol, 3-methyl-1,3-butandiol, 3-methyl-2-butene-1-ol, 3-methyl-3-butene-1-ol, 3-methyl-1-butene-3-ol, methyl isopropyl ketone, 2-methyl-butanal, methyl tertiary butyl formal, 4,4-dimethyl-1,3-dioxane, 4-methyl-5,6-dihydro-2H-pyran, and the like.

In the practice of the invention, it is possible to perform the reaction while feeding, as desired, a low-boiling compound inert under the reaction conditions, together with the reactants, into the acidic aqueous solution. The low-boiling inert compound mentioned above includes those compounds which do not undergo substantial change in nature during the reaction, such as hydrocarbons containing 1 to 10 carbon atoms, typical representatives of which are n-propane, n-butane, n-hexane and cyclohexane, and inert gases such as nitrogen.

The preferred rate of feeding FA to the reaction zone is decided taking into consideration the acidity of the acidic aqueous solution in the reaction zone, the reaction temperature and the pressure in reaction system. For increasing said FA feeding rate, it is necessary to increase the acidity of the acidic aqueous solution or raise the reaction temperature, and in that case there arises the problem of corrosion of the reaction vessel. Generally, therefore, the FA-feeding rate is preferably selected at a level not exceeding 3 moles (as formaldehyde) per kilogram of the acidic aqueous solution per hour. Although there is no lower limit in a strict sense on the FA-feeding rate, the formaldehyde source-feeding rate should preferably be not less than 0.2 mole (as formaldehyde) per kilogram of the acidic aqueous solution per hour because excessively small feeding rates require enlarged reaction vessel sizes, which are disadvantageous from the equipment viewpoint.

The reaction temperature which is preferred in practicing the present invention is generally selected within the range of 150-220° C. taking into consideration the acidity of the acidic aqueous solution in the reaction zone. Reaction temperatures below 150° C. result in decreased selectivity to isoprene even when the acidity of the acidic aqueous solution is increased so as to maintain the reaction rate at a constant level. Reaction temperatures exceeding 220° C. result in decreased conversion of formaldehyde under the conditions which give a maximal selectivity to isoprene, although the decrease in isoprene selectivity is not remarkable. When the reaction conditions are selected in a manner such that a high formaldehyde conversion can be attained, the isoprene yield decreases as a result of secondary reactions of isoprene.

The catalyst to be used in the process according to the present invention includes acidic substances such as inorganic acids, organic acids, and salts thereof. These are used in the reaction zone in the form of an aqueous solution. The preferable concentration of said aqueous solution depends on the kind of the acidic substance, the reaction temperature and the FA-feeding rate, among others but generally is selected such that the acidic aqueous solution has a pH of 0.5. to 2.5. When the pH of the acidic aqueous solution exceeds 2.5, a remarkable decrease in isoprene yield will result, whereas when said pH is below 0.5, remarkable corrosion of the reaction apparatus may result in addition to a remarkable decrease in isoprene yield. Preferred species of said acidic substance are low-volatile or nonvolatile ones and include inorganic acids, such as phosphoric acid, sulfuric acid and boric acid, heteropolyacids, such as tungstosilicic acid and tungstophosphoric acid, organic acids, such as p-toluenesulfonic acid, benzenesulfonic acid, trifluoromethanesulfonic acid and oxalic acid, and acidic salts, such as sodium hydrogen sulfate. These acidic substances may be used in combination of two or more of them. The combination of boric acid and phosphoric acid is especially recommendable. Preferably, an aqueous mixed acid solution containing 15–30 percent by weight of boric acid and 0.5–5 percent by weight of phosphoric acid is used, whereby a high isoprene yield can be obtained and at the same time the corrosiveness can be much reduced as compared with the use of phosphoric acid having the same concentration. When the boric acid concentration in the above mixed aqueous solution is below 15 percent by weight, the corrosiveness may increase. When the boric acid concentration exceeds 30 percent by weight, the isoprene yield will decrease. On the other hand, when the phosphoric acid concentration is below 0.5 percent by weight, an increased reaction temperature is required for achieveing a practical reaction rate and as a result the corrosiveness-reducing effect becomes small. When the phosphoric acid concentration exceeds 5.0 percent by weight, a satisfactory corrosiveness-reducing effect cannot be obtained although the corrosion is inhibited to a certain extent as compared with the case in which phosphoric acid is used alone.

The results of stainless steel corrosion test in an aqueous phosphoric acid solution and in a mixed aqueous solution of phosphoric acid and boric acid are shown below in Table A. The tests were conducted in the following manner.

A 1,000-ml pressure vessel made of glass equipped with thermometer, pressure gauge and magnetic stirrer was charged with 600 g of an aqueous acid solution having the composition indicated in Table A. Formaldehyde was added to the aqueous acid solution to a concentration of 3,000 ppm so as to simulate the reaction conditions in the actual reaction system. An SUS316 stainless steel testpiece (5 cm×1 cm×0.3 cm) was polished with No. 240 sandpaper and then with No. 1,000 sandpaper, washed in sequence with water, methyl alcohol and ethyl alcohol, and fixed on a thermometer with a teflon yarn. The atmosphere was purged with nitrogen gas and, then, maintained at 178° C. for 24 hours with stirring at 300 revolutions per minute. After cooling the vessel to room temperature, the testpiece was taken out, washed in sequence with water, methyl alcohol and ethyl alcohol, and dried. For the testpiece, the surface area, weight loss (weights before and after the test) and corrosion rate were measured.

For comparison, the results of corrosion tests (Experiments Nos. 6 and 7) performed in the same manner except that sulfuric acid was used in place of phosphoric acid are also shown in Table A. In that case, the corrosion rate was rather greater in mixed acid systems and the rate was acid concentration-dependent.

TABLE A

| Experiment No. | | Aqueous acid solution | | Test results | | |
|---|---|---|---|---|---|---|
| | | Phosphoric acid concentration (wt %) | Boric acid concn. (wt %) | Surface area (cm$^2$) | Weight loss (mg) | Corrosion rate (mm/year) |
| 1 | | 1.0 | 25.0 | 12.5 | 2.0 | 0.07 |
| 2 | | 1.0 | 0 | 11.0 | 5.7 | 0.24 |
| 3 | | 4.0 | 20.0 | 11.7 | 2.8 | 0.11 |
| 4 | | 4.0 | 0 | 12.6 | 11.6 | 0.42 |
| 5 | | 4.0 | 10.0 | 11.6 | 29.4 | 1.17 |
| 6 | Sulfuric | 0.4 | 20.0 | 17.8 | 228.9 | 16.81 |

TABLE A-continued

| Experiment No. | | Aqueous acid solution | | Test results | | |
|---|---|---|---|---|---|---|
| | | Phosphoric acid concentration (wt %) | Boric acid concn. (wt %) | Surface area (cm²) | Weight loss (mg) | Corrosion rate (mm/year) |
| 7 | acid Sulfuric acid | 0.4 | 0 | 17.8 | 186.7 | 14.57 |

Since isobutene which is formed from ATBE under the reaction conditions has a critical temperature of 144.7° C. and is in the gaseous form under the reaction conditions, it is required, in performing the reaction, to dissolve the gaseous isobutene efficiently in the acidic aqueous solution. For this purpose, it is sufficient to cause efficient gas-liquid contact, for example by vigorous stirring of the acidic aqueous solution, with a baffle plate or plates inserted as necessary. For this purpose, it is efficient to further make coexist in the reaction zone a glycol ether of the general formula

(I)

wherein $R^1$ is a hydrogen atom or a methyl group, $R^2$ and $R^3$ each is a hydrogen arom or an alkyl group containing 1 to 4 carbon atoms and n is an integer of 2 to 15 provided that at least one of $R^1$, $R^2$ and $R^3$ is an alkyl group and that the total number of carbon atoms contained in the formula is at least 8. Thus, addition of said glycol ether to the acidic aqueous solution in the reaction zone brings about smooth contact between isobutene with the acidic aqueous solution in the reaction zone, whereby an increased isoprene yield is brought about. Said glycol ether is added generally in an amount of about 5 to 15 percent by weight based on the acidic aqueous solution. The improvement in contact between isobutene and the acidic aqueous solution as caused by the addition of the glycol ether is presumably due to the fact that said glycol ether has excellent compatibility with both isobutene and the acidic aqueous solution.

Referring to general formula (I), examples of the alkyl group containing 1 to 4 carbon atoms as $R^2$ and $R^3$ are methyl, ethyl, n-propyl, isopropyl and n-butyl. It is necessary that at least one of $R^1$, $R^2$ and $R^3$ is an alkyl group. If $R^1$, $R^2$ and $R^3$ are at the same time hydrogen atoms, the compatibility of the glycol ether to isobutene becomes reduced so that the effect of addition thereof cannot be expected any more. In general formula (I), n is required to be an integer of 2 to 15. If n is 1, the effect of addition cannot be expected as in the case in which $R^1$, $R^2$ and $R^3$ are each at the same time a hydrogen atom and moreover the glycol ether is disadvantageously distilled off during the reaction. If n exceeds 15, the compatibility of the glycol ether to the acidic aqueous solution disadvantageously becomes reduced. The total number of carbon atoms contained in general formula (I) is required to be at least 8, so that the kind of each of $R^1$, $R^2$ and $R^3$ and the value of n should be decided so as to meet this requirement. When the total number of carbon atoms is smaller than 8, the glycol ether has a decreased compatibility to isobutene, which results in a decreased effect of addition of the glycol ether, and moreover is disadvantageously distilled off during the reaction.

Preferred examples of the glycol ether are polypropylene glycol having an average molecular weight of 700, tripropylene glycol monomethyl ether, tetraethylene glycol dimethyl ether, diethylene glycol diethyl ether and diethylene glycol monobutyl ether.

When the reaction is conducted for a prolonged period of time, high-boiling byproducts formed in trace amounts during the reaction, especially tar-like substances, are accumulated in the acidic aqueous solution. The high-boiling point byproducts may be separated from the acidic aqueous solution containing high-boiling byproducts accumulated in the reaction zone (it is sometimes referred to as "reaction mixture" in the following description), for example by allowing the reaction mixture to stand in the reaction vessel or by taking out a part of the reaction mixture and transferring the same to a decanter, for instance, followed by separation of the high-boiling byproducts therein. However, since the high-boiling byproducts are close in specific gravity to the acidic aqueous solution, it is difficult to separate them by treating the reaction mixture as it is by the conventional method making use of the difference in specific gravity, such as decantation. Moreover, since said high-boiling byproducts have a property of solidifying at room temperature, their handling after separation is very troublesome. Therefore, the use of a diluent having a low specific gravity is recommendable in the separation of the high-boiling byproducts. Preferable as such diluent is the residue obtained from the organic layer resulting from condensation of the vapor from the reaction zone by distilling off the unreacted starting materials, isobutene, tertiary butanol and isoprene from said organic layer or part thereof (hereinafter each referred to simply as "solvent"), for this solvent is a byproduct from the process according to the invention, therefore is well compatible with the above-mentioned high-boiling byproducts and does not require any particular consideration for the separation and recovery thereof. More particularly, said solvent is obtained as the residue after removal of the unreacted starting materials, isobutene, tertiary butanol and isoprene from the distillate organic layer coming from the reaction zone by distillation and contains, among others, 4-methyl-5,6-dihydro-2H-pyran, methyl isopropyl ketone, 2-methylbutanal, 2,6-dimethyl-2,5-heptadiene, 2,6-dimethyl-1,5-heptadiene, 3-methyl-3-buten-1-ol and 2-methyl-3-buten-2-ol. Furthermore, it contains compounds containing 4 to 15 carbon atoms and having such functional groups as hydroxyl, carbonyl, ether linkage and carbon-to-carbon double bond. This distillation residue may be used as it is as the solvent, or part thereof may be separated therefrom and the remaining portion may be used as the solvent.

There is no particular limitation on the amount of the solvent. However, too small an amount will results in a small difference in specific gravity between the solution containing the high-boiling byproducts dissolved therein and the acidic aqueous solution, and in an increased viscosity of said solvent, which is disadvantageous from the processability standpoint. When the solvent is added in an excessive amount, isoprene and other desired components dissolved in the acidic aqueous solution are extracted with the solvent and a recovery procedure of isoprene and other desired components becomes necessary. From these viewpoints, the solvent is added generally in an amount of 20 to 500 g per kilogram of formaldehyde to be fed or, more specifically, in an amount of 0.5 to 3 times the weight of the high-boiling byproducts formed.

The separation of the high-boiling byproducts from the acidic aqueous solution using the solvent can be effected, for instance, by allowing the reaction mixture in the reaction vessel, or by extracting a part of the reaction mixture and transferring to a decanter, extraction tower or the like, where the high-boiling byproducts are separated. The place where the solvent is to be added can be selected depending on the separation method employed.

In practicing the invention on an industrial scale, it is necessary to supply heat by an appropriate means, for instance by circulating the acidic aqueous solution existing in the reaction vessel through a heat exchanger disposed outside the reaction vessel, since heat is required in large amounts for effecting the reaction and distilling off isoprene, water and other low-boiling components. However, when said acidic aqueous solution is heated by circulating the same through an external heat exchanger, the temperature of the acidic aqueous solution in the heat exchanger rises to a level exceeding the optimal reaction condition. As a result, side reactions proceed to an increased extent within the heat exchanger and eventually a decrease in isoprene yield results. It has now been found that this problem can be solved by feeding at least a part of the isobutene source to be subjected to reaction, together with the acidic aqueous solution taken out from the reaction vessel, to the heat exchanger and, after heating, introducing the isobutene source-aqueous solution mixture into the reaction vessel. The minimum amount of the isobutene source to be fed to the heat exchanger depends on the amount of heat to be supplied to the heat exchanger. Besides the temperature rise in the acidic aqueous solution in the heat exchanger, the difference, among others, in comparison with regard to the starting materials and product between the reaction vessel inside and the heat exchanger is also a factor causing side reactions to proceed within the heat exchanger. To solve this problem, the heat exchanger volume should preferably be as small as possible. For that reason, the amount of heat to be given in the heat exchanger should preferably be as small as possible. The heat energy required for the progress of the reaction and the heat energy required for distilling off isoprene, water and other low-boiling components vary depend on whether the starting materials are in the gaseous or liquid form. When all the starting materials are fed to the reaction zone wholly in the gaseous form, the amount of heat to be given is minimal. However, experiments performed by the present inventors revealed that when an aqueous formaldehyde solution employed as the formaldehyde source is vaporized and introduced into a reactor, formaldehyde consumption takes place during the vaporization. In view of the above fact, it is preferable to feed the aqueous formaldehyde solution to the reaction zone in the liquid form, while BYIB and water (exclusive of the water contained in the aqueous formaldehyde solution) are preferably fed to the reaction zone in the gaseous form. By doing so, the heat energy to be given in the heat exchanger can advantageously be reduced.

As is mentioned above, the reaction in the process according to the present invention is carried out by feeding the isobutene source, FA and water into the acidic aqueous solution either continuously or intermittently while distilling off isoprene, together with water, unreacted starting materials, isobutene, tertiary butanol and other low-boiling components from the reaction zone. Since the isobutene source is used in excess over FA and water is also used in the process, the excess the isobutene source and water are distilled off, together with isoprene, from the reaction zone. Therefore, in the process according to the invention on a commercial scale, a large amount of heat is released from the reaction zone in company with the vapor therefrom. Such a large amount of heat can be recovered effectively and very efficiently in the following manner: First, the vapor from the reaction zone, especially water vapor contained therein, is condensed, whereby the heat energy possessed of by the vapor is recovered. Then, the heat energy possessed of by the uncondensed vapor from the reaction zone is used as the heat source for vaporizing the isobutene and/or the heat source for recovering the isobutene by distillation from the organic layer obtained from the condensate of the vapor from the reaction zone by phase separation.

In recovering the heat energy possessed of by the vapor from the reaction zone, the vapor from the reaction zone is allowed to condense stepwise under almost the same pressure as in the reaction zone, whereby the heat energy possessed of by said vapor from the reaction zone is recovered effectively. Thus, the above-mentioned vapor from the reaction zone is first allowed to condense partly at a temperature adequate for the condensation of water in said vapor from the reaction zone, whereby the latent heat of water is recovered and at the same time the sensible heat of the vapor from the reaction zone is recovered. The heat recovery can be effected by subjecting the vapor from the reaction zone to heat exchange with water to produce steam or by directly using the vapor from the reaction zone as the heat source for reboiler of a distillation column to be used in the recovery of isobutene, the recovery of ATBE, tertiary butanol or in the recovery or purification of isoprene by introducing said vapor into said reboiler. The amount of steam which can be produced by heat exchange between the vapor from the reaction zone and water is almost equal in weight to the amount of water contained in said vapor, and the steam so generated can be used as the heat source for recovering isobutene, ATBE, tertiary butanol or isoprene or for purifying isoprene. In the heat exchange between the vapor from the reaction zone and water, steam portions differing in pressure and therefore useful for different purposes can be produced when said vapor from the reaction zone is condensed multistepwise.

Of the water obtained by partial condensation of the vapor from the reaction zone, a necessary amount is generally recycled to the reaction vessel while the remaining portion of water is sent to a step of recovering unreacted reactants, in which step tertiary butanol and formaldehyde are recovered.

The heat energy of the uncondensed portion of the vapor from the reaction zone is used as the heat source for vaporizing isobutene and/or for recovering the isobutene by distillation from the organic layer obtained from the condensate of the vapor from the reaction zone by phase separation. the vaporization of the isobutene can be effected by subjecting ATBE and isobutene to heat exchanger with the uncondensed portion of the vapor from the reaction zone. Feeding the vaporized isobutene to the reaction vessel causes reduction in the heat load on the heat exchanger attached to the reaction vessel and furthermore facilitates the dispersion of isobutene into the acidic aqueous solution. A method generally used for supplying a necessary amount of heat to a reactor comprises circulating a reaction mixture through a heat exchanger disposed externally to the reactor. When vaporized isobutene is fed to the reactor through said heat exchanger, as mentioned above, the heat exchanger temperature required for the evaporation of the acidic aqueous solution can be lowered. The heat of condensation obtainable form the uncondensed portion of the vapor from the reaction zone before or after use thereof for the vaporization of isobutene can be used as the heat source for recovering isobutene from isobutene-containing organic layer by distillation. Said isobutene-containing organic layer can be obtained by phase separation of the condensate of that portion of the vapor from the reaction zone which remains after partial condensation of said vapor, which condensate results from the use of said vapor portion as the heat source for vaporizing isobutene or for recovering unreacted isobutene by distillation. Besides said organic layer, an aqueous layer is obtained at the same time. This aqueous layer is sent to a step of recovering unreacted reactants, where tertiary butanol and formaldehyde are recovered. Since most of the heat required for distilling off water from the reaction zone can be recovered by partially condensing the vapor from the reaction zone, the amount of heat required to produce a unit amount of isoprene is decided by the ratio C/F between the reactants to be fed to the reaction zone. Thus, the amount of the isobuene source fed to the reaction zone determines the amount of heat required for the vaporization of isobutene and the recovery of ATBE, isobutene and tertiary butanol.

By way of example, a system for the heat recovery from the vapor from the reaction zone is illustrated in FIG. 1.

The vapor from a reactor (1) is introduced into heat exchangers (3) and (3'), where steam is generated. Of the water condensed in (3) and (3'), a required amount is recycled to the reactor and the remaining portion sent to step or recovering ATBE, tertiary butanol and FA. The uncondensed portion of the vapor from the reaction zone, which comes from (3) and (3'), is introduced into a heat exchanger (4), where part of said uncondensed portion is condensed, whereby isobutene is vaporized. ATBE and the vaporized isobutene are fed to a heat exchanger (2) disposed externally to the reactor. That portion of the vapor from the reaction zone which remains still uncondensed and comes from (4) is introduced into a heat exchanger (5). The condensate formed in (4) is led to a decanter (6), where the condensate separates into an organic layer and an aqueous layer. The organic layer is preheated in (5) and then fed to a distillation column (7), where isobutene is recovered. The aqueous layer is sent to a step (I) of recovering ATBE, tertiary butanol and FA. The condensate formed in (5) is led to (6) and is separated into an organic layer and an aqueous layer as in the case of the condensate formed in (4) The bottom liquid from (7) is sent to a step (II) of recovering and purifying isoprene and recovering tertiary butanol.

The process according to the present invention produces highly pure isoprene, which is very useful as the starting material for the manufacture of polyisoprene and terpenes and terpenoid compounds, among other.

Having generally described this invention, a further understanding can be obtained by reference to certain specific examples which are provided herein for purpose of illustration only and are not intended to be limitative of this invention unless otherwise specified.

EXAMPLE 1

The reaction apparatus used was a 750-ml pressure reactor made of glass and equipped with raw material inlet tubes, water inlet tube, thermometer, baffle plate (bubbler), magnetic stirrer and vapor outlet tube. With the vapor outlet tube, there were connected two distillate receptacles (one for preliminary run and the other for quantitative determination) via a condenser. The reactor was charged with 300 g of 7.5% (by weight) aqueous phosphoric acid, and the contents were heated at 168° C. under a pressure of 10.7 kg/cm$^2$. The vapor pressure of 7.5% (by weight) aqueous phosphoric acid at 168° C. is 7.5 kg/cm$^2$. To the reactor, there were fed methyl tertiary butyl ether (hereinafter referred to as "MTBE") at the rate of 130 ml/hr, 4.88% (by weight) aqueous formaldehyde at the rate of 27 ml/hr, and water at the rate of 31.8 ml/hr, while the reactor contents were stirred at the rate of 1,000 revolutions per minute at the above temperature and pressure. The vapor coming out of the reactor was condensed in the condenser and collected in the distillate receptacle for preliminary run. After the reaction was conducted under the above conditions for 2 hours, the distillate passage was changed to the distillate receptacle for quantitative determination and sampling was performed for 1.25 hours. To constantly maintain the pressure, the vapor was withdrawn through a purge valve and, in sampling, the purged gas was introduced into a trap cooled with dry ice and acetone, where the gas was caused to be absorbed by n-butyl ether. During the above sampling hours, the pressure, temperature and liquid level were kept almost constant.

The distillate in the receptacle for quantitative determination was allowed to separate into an aqueous phase and an organic phase, and both the phases were analyzed. The aqueous layer was analyzed for formaldehyde content by the sodium sulfite method and for methanol, tertiary butanol, MTBE and isobutene contents by gas chromatography (internal standard method). The organic layer was analyzed for isobutene, MTBE tertiary butanol, methanol isoprene and by-products contents by gas chromatography (internal standard method). The liquid collected in the trap was also analyzed for isobutene, MTBE and isoprene contents by gas chromatography (internal standard method). The results were as follows:

| | |
|---|---|
| MTBE fed | 120.2 g (1366 millimoles) |
| Formaldehyde fed | 5.24 g (175 millimoles) |
| Water fed | 102.2 g (5680 millimoles) |
| Isobutene distilled off | 5.21 g (930 millimoles) |
| MTBE distilled off | 101.7 g (156 millimoles) |
| Tertiary butanol distilled off | 9.50 g (128 millimoles) |
| Formaldehyde distilled off | 0.257 g (8.6 millimoles) |
| Isoprene distilled off | 8.23 g (121 millimoles) |
| Methanol distilled off | 38.7 g (1210 millimoles) |
| Water distilled off | 105.0 g (5830 millimoles) |
| MTBE/FA | 7.8 |
| Formaldehyde feed rate per kg | 0.47 |

-continued

| of acidic aqueous solution (moles/hr) | |
|---|---|
| Formaldehyde conversion (%) | 9.1 |
| Isoprene selectivity (%) | |
| Formaldehyde basis | 72.7 |
| MTBE basis | 79.6 |

The isoprene selectivity based on MTBE is calculated on the basis of number of moles which subtract number of moles of produced isobutene and tertiary butanol from number of moles of consumed MTBE.

EXAMPLE 2 to EXAMPLE 12

Using the same apparatus as used in Example 1, the procedure of Example 1 was followed except that the reaction conditions were varied. The results obtained are shown in Table 1.

moles/hr) and 73.1 g/hr (0.23 mole/hr), respectively. After the entering of the aqueous vapor from the first reactor into the second reactor was confirmed, 45.4% (by weight) aqueous formaldehyde was fed to the second reactor at the rate of 15.2 g/hr (0.23 mole/hr). The reaction was carried out in this manner for 2.5 hours while stirring at 1,000 revolutions per minute at the above-specified pressure and temperature. The aqueous vapor from the second reactor was condensed in a condenser and collected in a receptacle. The pressure was kept constant by fine control by means of purging the nitrogen gas within the system. The liquid level of the acidic aqueous solution was almost constant during the reaction. The distillate collected in the receptacle during the period beginning from 1.5 hours from the start of the reaction and the time of completion of the reaction as well as the substance accompanied by the purged

TABLE 1

| Example | 2 | 3 | 4 | 5 | 6 | 7 | 8 | 9 | 10 | 11 | 12 |
|---|---|---|---|---|---|---|---|---|---|---|---|
| Acid | Phosphoric acid | Phosphoric acid | Phosphoric acid | Phosphoric acid | Phosphoric acid | Phosphoric acid | Phosphoric acid | Sulfuric acid | Sulfuric acid | Tungstosilicic acid | p-Toluene sulfonic acid |
| Acid concentration (wt %) | 7.5 | 7.5 | 7.5 | 3.0 | 3.0 | 3.0 | 7.5 | 1.0 | 3.6 | 2.5 | 3.0 |
| Temperature (°C.) | 168 | 168 | 168 | 178 | 178 | 178 | 168 | 168 | 180 | 168 | 168 |
| Vapor pressure of acidic aqueous solution [Pw] (kg/cm$^2$) | 7.5 | 7.5 | 7.5 | 9.6 | 9.6 | 9.6 | 7.5 | 7.6 | 8.7 | 7.6 | 7.6 |
| Reaction pressure [P] (kg/cm$^2$) | 10.6 | 14.0 | 17.5 | 12.2 | 16.0 | 17.9 | 21.8 | 17.5 | 19.2 | 13.7 | 13.7 |
| P/Pw | 1.41 | 1.87 | 2.33 | 1.27 | 1.67 | 1.86 | 2.91 | 2.30 | 2.21 | 1.80 | 1.41 |
| MTBE/FA (moles/mole) | 8.1 | 10.0 | 10.0 | 6.0 | 5.0 | 12.0 | 10.0 | 10.0 | 10.0 | 10.1 | 10.0 |
| Formaldehyde feeding rate (moles/kg · hr) | 0.78 | 0.76 | 1.35 | 0.32 | 0.29 | 0.77 | 1.73 | 0.76 | 0.36 | 0.76 | 0.78 |
| Distillate water/MTBE fed (moles/mole) | 3.8 | 2.3 | 1.5 | 7.5 | 3.0 | 2.3 | 1.0 | 1.5 | 1.6 | 2.4 | 2.4 |
| Formaldehyde conversion (%) | 90.7 | 94.7 | 95.9 | 85.8 | 97.8 | 93.8 | 97.6 | 96.9 | 97.6 | 93.9 | 95.2 |
| Isoprene selectivity (%) (formaldehyde basis) | 66.5 | 72.2 | 69.7 | 68.1 | 67.2 | 73.4 | 69.6 | 73.1 | 69.5 | 70.5 | 71.5 |
| Isoprene selectivity (%) (MTBE basis) | 78.8 | 79.2 | 77.0 | 78.0 | 68.8 | 80.5 | 74.5 | 74.6 | 71.4 | 77.3 | 77.9 |

EXAMPLE 13

The reaction apparatus used was composed of two 750-ml pressure glass reaction vessels connected to each other by means of a thermally insulated pipe (for vapor). Each reaction vessel (reactor) was equipped with MTBE inlet tube (for the second reactor, inlet tube for the vapor from the first reactor), aqueous formaldehyde solution inlet tube, baffle plate, thermometer and magnetic stirrer.

Each of the above two reactors was charged with 300 g of 7.5% (by weight) aqueous phosphoric acid. The contents in the first reactor were heated at 168° C. at a pressure of 18.2 kg/cm$^2$ and the contents in the second reactor at the same temperature at a pressure of 17.3 kg/cm$^2$. The vapor pressure of 7.5% (by weight) phosphoric acid at 168° C. was 7.5 kg/cm$^2$. To the first reactor, there were fed MTBE and 9.44% (by weight) aqueous formaldehyde at the rates of 210 g/hr (2.76 nitrogen gas (substance introduced into a dry ice-acetone trap and absorbed by n-butyl ether therein) was analyzed for evaluation of the reaction results.

Thus, the distillate was allowed to separate into an aqueous phase and an organic phase. The aqueous phase was subjected to gas chromatography (internal standard method) and also analyzed for unreacted formaldehyde by the sodium sulfite method. The organic layer and the substance in the above-mentioned trap were analyzed by gas chromatography (internal standard method). The results obtained are shown in Table 2.

EXAMPLE 14–16

The reaction was carried out in the same manner and under the same conditions as in Example 13 using the same apparatus as used in Example 13 except that the ratio of isobutene fed to formaldehyde fed and according the water feeding rate were varied. The results obtained are shown in Table 2.

TABLE 2

| | Example 13 | | Example 14 | | Example 15 | | Example 16 | |
|---|---|---|---|---|---|---|---|---|
| | First reactor | Second reactor | First reactor | Second reactor | First reactor | Second reactor | First reactor | Second reactor |
| Reaction pressure [P] (kg/cm$^2$) | 18.2 | 17.3 | 17.9 | 17.3 | 15.1 | 14.7 | 15.3 | 14.8 |
| P/Pw | 2.4 | 2.3 | 2.4 | 2.3 | 2.0 | 2.0 | 2.0 | 2.0 |
| Feeding rate | | | | | | | | |
| MTBE (moles/hr) | 2.76 | — | 3.68 | — | 3.65 | — | 2.75 | — |
| Formaldehyde | 0.23 | 0.23 | 0.23 | 0.23 | 0.23 | 0.23 | 0.23 | 0.23 |

TABLE 2-continued

| | Example 13 | | Example 14 | | Example 15 | | Example 16 | |
|---|---|---|---|---|---|---|---|---|
| | First reactor | Second reactor | First reactor | Second reactor | First reactor | Second reactor | First reactor | Second reactor |
| (moles/hr) | | | | | | | | |
| Water (moles/hr) | 3.68 | 0.46 | 5.06 | 0.46 | 6.90 | 0.46 | 5.01 | 0.46 |
| MTBE/FA (moles/mole) | 6.0 | | 8.0 | | 8.0 | | 6.0 | |
| Formaldehyde conversion (%) | 98.4 | | 97.9 | | 96.4 | | 97.2 | |
| MTBE conversion (%) | 94.5 | | 94.2 | | 91.6 | | 91.8 | |
| Isoprene selectivity (%) (formaldehyde basis) | 70.8 | | 73.9 | | 73.6 | | 71.2 | |
| Isoprene selectivity (%) ($C_4$ basis)* | 72.8 | | 76.4 | | 79.3 | | 76.4 | |

*The isoprene selectivity based on MTBE is calculated on the basis of number of moles which subtract number of moles of produced isobutene and tertiary butanol from number of moles of consumed MTBE.

EXAMPLE 17-19

The reaction was carried out in the same manner and under the same conditions as in Example 13 except that 1.0% (by Weight) aqueous sulfuric acid was used in place of aqueous phosphoric acid, the reaction pressure, MTBE and aqueous formaldehyde feeding rates and the concentration of the aqueous formaldehyde were varied as indicated in Table 3. The results obtained are shown in Table 3.

TABLE 3

| | Example 17 | | Example 18 | | Example 19 | |
|---|---|---|---|---|---|---|
| | First reactor | Second reactor | First reactor | Second reactor | First reactor | Second reactor |
| aqueous acid* | 1% Sulfuric acid | 1% Sulfuric acid | 1% Sulfuric acid | 1% Sulfuric acid | 1% Sulfuric acid | 1% Sulfuric acid |
| [Pw] | 7.7 | 7.7 | 7.7 | 7.7 | 7.7 | 7.7 |
| Reaction pressure [P] (kg/cm$^2$) | 14.2 | 13.7 | 13.0 | 12.7 | 15.2 | 14.9 |
| P/Pw | 1.8 | 1.8 | 1.7 | 1.6 | 2.0 | 1.9 |
| Feeding rate | | | | | | |
| MTBE (moles/hr) | 1.20 | — | 0.88 | — | 4.60 | — |
| Formaldehyde (moles/hr) | 0.15 | 0.15 | 0.11 | 0.11 | 0.23 | 0.23 |
| Water (moles/hr) | 2.70 | 0.30 | 2.42 | 0.22 | 8.74 | 0.46 |
| MTBE/FA in each reactor (moles/mole) | 4.0 | | 4.0 | | 4.0 | |
| Formaldehyde conversion (%) | 97.5 | | 97.6 | | 95.6 | |
| MTBE conversion (%) | 94.2 | | 94.5 | | 90.1 | |
| Isoprene selectivity (%) (formaldehyde basis) | 68.9 | | 69.7 | | 75.0 | |
| Isoprene selectivity (%) ($C_4$ basis) | 73.0 | | 72.8 | | 81.0 | |

*each of charged amounts is 300 g

EXAMPLE 20

The reaction apparatus used was composed of three 750-ml pressure glass vessels (reactors) connected in series with piping for the passage of vapor under thermal insulation. Each reactor was equipped with MTBE inlet tube(for the second and the third reactor, inlet tube for vapor from the first and the second reactor, respectively), aqueous formaldehyde inlet tube, baffle plate, thermometer and magnetic stirrer.

Each of the above three reactors was charged with 300 g of 7.5% (by weight) aqueous phosphoric acid, and the contents were heated at 168° C. and at a pressure indicated in Table 4. The above pressure levels were maintained by introducing nitrogen gas and inserting valves between the first and the second reactor and between the second and the third reactor.

To the first reactor MTBE and 3.65% (by weight) aqueous formaldehyde were fed at the rates of 420 g/hr (5.53 moles/hr) and 190 g/hr (0.23 mole/hr), respectively. After the entering of the aqueous vapor from the first reactor into the second reactor was confirmed, 45.4% (by weight) aqueous formaldehyde was fed to the second reactor at the rate of 15.2 g/hr (0.23 mole/hr). Similarly, after confirming the entrance of the aqueous vapor from the second reactor into the third reactor, 45.5% (by weight) aqueous formaldehyde was fed to the third reactor at the rate of 15.2 g/hr (0.23 mole/hr). The reaction was carried out in this manner for 2.5 hours while stirring the contents of each reactor at 1,000 revolutions per minute at the above-mentioned pressure and temperature. The aqueous vapor from the third reactor was condensed in the condenser and collected in the receptacle. The pressure in each reactor was kept constant by fine adjustment by purging the nitrogen gas. The surface of the acidic aqueous solution in each reactor remained at an almost constant level during the reaction. The reaction results obtained in the same manner as in Example 13 are shown in Table 4.

EXAMPLE 21

The reaction apparatus used was composed of four 750-ml pressure glass reaction vessels (reactors) connected in series by means of piping for the passage of vapor under thermal insulation. Each reactor was equipped with MTBE inlet tube (for the second, third and fourth reactor, inlet tube for the vapor from the preceding reactor), aqueous formaldehyde inlet tube, baffle plate, thermometer and magnetic stirrer.

Each of the above four reactors was charged with 300 g of 7.5% (by weight) aqueous phosphoric acid and heated at 168° C. and at a pressure indecated in Table 4. The above pressure was maintained by introducing nitrogen gas and inserting a valve between every two neighboring reactors.

To the first reactor, there were fed MTBE and 2.79% (by weight) aqueous formaldehyde at the rates of 560 g/hr (7.37 moles/hr) and 246 g/hr (0.23 mole/hr), respectively. After confirming the entering of the aqueous vapor from the first reactor into the second reactor, 45.4% (by weight) aqueous formaldehyde was fed to the second reactor at the rate of 15.2 g/hr (0.23 mole/hr). Similarly, after confirming the entering of the aqueous vapor from the second reactor into the third reactor, 45.5% (by weight) aqueous formaldehyde was fed to the third reactor at the rate of 15.2 g/hr (0.23 mole/hr). Furthermore, after confirming the entering of the aqueous vapor from the third reactor into the fourth reactor, 45.5% (by weight) aqueous formaldehyde was fed to the fourth reactor at the rate of 15.2 g/hr (0.23 mole/hr). The reaction was carried out in that manner for 2.5 hours while stirring the contents of each reactor at 1,000 revolutions per minute at the above-specified pressure and temperature. The aqueous vapor from the fourth reactor was condensed in the condenser and collected in the distillate receptacle. The pressure in each reactor was kept constant by fine adjustment thereof by purging the nitrogen gas. The acid aqueous solution surface remained at an almost constant level during the reaction. The reaction results obtained in the same manner as in Example 13 are shown in Table 4.

What we claim is:

1. A process for producing isoprene by reacting an alkyl tertiary butyl ether with formaldehyde in an acidic aqueous solution, characterized in:

(a) that the acidic aqueous solution is present in the reaction zone, (b) that said alkyl tertiary butyl ether, a formaldehyde source and water are fed to said reaction zone continuously or intermittently, and (c) that isoprene, water, unreacted starting materials, isobutene, tertiary butanol and other low-boiling components are distilled off from said reaction zone, the amounts of said alkyl tertiary butyl ether and formaldehyde source being fed to said reaction zone being such that the alkyl tertiary butyl ether-to-formaldehyde molar ratio in the charge is at least 2 and the pressure in the reaction system being maintained at a level 1.2 to 3.5 times the vapor pressure at the reaction temperature of the acidic aqueous solution existing in the reaction zone, said alkyl tertiary butyl ether-to-formaldehyde molar ratio being calculated by calculating the amount of the formaldehyde source in formaldehyde equivalent when said source is other than formaldehyde.

2. The process as claimed in claim 1, characterized in:

(a) that the acidic aqueous solution is present in plural reaction zones connected in series, (b) that an alkyl tertiary butyl ether is fed to the first reaction zone continuously or intermittently while a formaldehyde source and water are fed to each reaction zone continuously or intermittently, (c) that isoprene, water, unreacted starting materials, isobutene, tertiary butanol and other low-boiling components are distilled off from each reaction zone except the last one and fed to the subsequent reaction zone, and (c) that isoprene, water, unreacted starting materials, isobutene, tertiary butanol and other low-boiling components are distilled off from the last reaction zone, the amount of said alkyl tertiary butyl ether and formaldehyde source being fed to the first reaction zone being such that the alkyl tertiary butyl ether-to-formaldehyde molar ratio in the charge is at least 2, the amounts of said alkyl tertiary butyl ether, isobutene and/or tertiary butanol-to-formaldehyde molar ratio being fed to each reaction zone exclusive of the first reaction zone being such that said alkyl tertiary butyl ether, isobutene and/or tertiary butanol-to-formaldehyde molar ratio in the charge is at least 2, and the pressure in the reaction

TABLE 4

|  | Example 20 | | | Example 21 | | | |
| --- | --- | --- | --- | --- | --- | --- | --- |
|  | First reactor | Second reactor | Third reactor | First reactor | Second reactor | Third reactor | Fourth reactor |
| Reaction pressure [P] (kg/cm$^2$) | 15.2 | 14.9 | 14.6 | 15.5 | 15.2 | 14.9 | 14.6 |
| P/Pw | 2.0 | 2.0 | 1.9 | 2.1 | 2.0 | 2.0 | 1.9 |
| Feeding rate |  |  |  |  |  |  |  |
| MTBE (moles/hr) | 5.54 | — | — | 7.35 | — | — | — |
| Formaldehyde (moles/hr) | 0.23 | 0.23 | 0.23 | 0.23 | 0.23 | 0.23 | 0.23 |
| Water (moles/hr) | 1.01 | 0.46 | 0.46 | 13.3 | 0.46 | 0.46 | 0.46 |
| MTBE/FA in each reactor (moles/mole) |  | 8.0 |  |  | 8.0 | | |
| Formaldehyde conversion (%) |  | 96.4 |  |  | 96.4 | | |
| MTBE conversion (%) |  | 94.2 |  |  | 94.5 | | |
| Isoprene selectivity (%) (formaldehyde basis) |  | 74.5 |  |  | 74.9 | | |
| Isoprene selectivity (%) (C$_4$ basis) |  | 80.2 |  |  | 80.8 | | | system being maintained at a level 1.2 to 3.5 times the vapor pressure at the reaction temperature of the acidic aqueous solution existing in the reaction zone, said alkyl tertiary butyl ether, isobutene and/or tertiary butanol-to-formadehyde molar ratio being calculated by calculating the amount of the formaldehyde source in formaldehyde eqivalent when said source is other than formaldehyde.

3. The process as claimed in claim 1 or 2, wherein an alkyl group of the alkyl tertiary butyl ether has not more than 5 carbon atoms.

4. The process as claimed in claim 1 or 2, wherein the alkyl tertiary butyl ether is methyl tertiary butyl ether, ethyl tertiary butyl ether, n-propyl tertiary butyl ether, isobutyl tertiary butyl ether, n-amyl tertiary butyl ether, 3-methylbutyl tertiary butyl ether or 2-methylbutyl tertiary butyl ether.

5. The process as claimed in claim 1 or 2, wherein the alkyl tertiary butyl ether is methyl tertiary butyl ether.

6. The process as claimed in claim 2, wherein the number of the reaction zones is 2, 3 or 4.

7. The process as claimed in claim 1, wherein the feed rate of the formaldehyde source as expressed in terms of the number of moles of formaldehyde per kilogram of the acidic aqueous solution per hour is not more than 3 moles/kg·hr.

8. The process as claimed in claim 1, wherein an aqueous formaldehyde solution is used as the formaldehyde source.

9. The process as claimed in claim 1, wherein the reaction temperature is 150°–220° C.

10. The process as claimed in claim 1, wherein the acidic aqueous solution has a pH of 0.5–2.5.

11. The process as claimed in claim 1, wherein the acidic aqueous solution is an aqueous mixed acid solution containing 15–30 percent by weight of boric acid and 0.5–5 percent by weight of phosphoric acid.

12. The process as claimed in claim 1, wherein a glycol ether of the general formula

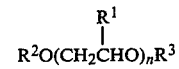

$$R^2O(CH_2CHO)_nR^3 \quad \text{(I)}$$
$$\overset{|}{R^1}$$

wherein $R^1$ is a hydrogen atom or a methyl group, $R^2$ and $R^3$ each is a hydrogen atom or an alkyl group containing 1 to 4 carbon atoms and n is an integer of 2 to 15, provided that at least one of $R^1$, $R^2$ and $R^3$ is an alkyl group and the total number of carbon atoms included in the above formula is at least 8, is added, in an amount of 5 to 15 percent by weight, to the acid aqueous solution.

13. The process as claimed in claim 8, wherein a part of the acidic aqueous solution is taken out from the reaction vessel, heated and returned to the reaction vessel, while feeding to the reaction vessel the aqueous formaldehyde solution to be newly fed in the liquid form and the alkyl tertiary butyl ether and water (exclusive of the water contained in the aqueous formaldehyde solution) in the gaseous form, each continuously or intermittently.

14. The process as claimed in claim 8, wherein a part of the acidic aqueous solution in taken out from the reaction vessel, heated together with at least a part of the alkyl tertiary butyl ether, isobutene and/or tertiary butanol to be fed and then introduced into the reaction vessel in admixture therewith.

15. The process as claimed in claim 1, wherein the residue obtained from the organic layer resulting from condensation of the vapor from the reaction zone by distilling off the unreacted starting materials and isoprene therefrom or a part of said residue is added to the acidic aqueous solution containing high-boiling byproducts accumulated in the reaction zone or a part thereof and the mixture is separated into an acidic aqueous solution and an organic layer containing extracted high-boiling byproducts.

16. The process as claimed in claim 1, wherein the vapor from the reaction zone, especially water vapor contained therein, is condensed, whereby the heat energy possessed of by the vapor is recovered, and the heat energy possessed of by the uncondensed vapor is used as the heat source for vaporizing isobutene and/or heat source for recovering isobutene by distillation from the organic layer obtained from the condensate of the vapor from the reaction zone by phase separation.

* * * * *

UNITED STATES PATENT AND TRADEMARK OFFICE
CERTIFICATE OF CORRECTION

PATENT NO. : 4,593,145
DATED : JUNE 3, 1986
INVENTOR(S) : NINAGAWA, YAMADA, RENGE, KYO, OSAKI, KUSHIDA

It is certified that error appears in the above-identified patent and that said Letters Patent is hereby corrected as shown below:

On the title page,

In Field [30], please insert

--March 12, 1984 [JP] Japan......59-47735

April 16, 1984, [JP] Japan.....59-77195--.

Signed and Sealed this

Thirtieth Day of December, 1986

Attest:

DONALD J. QUIGG

Attesting Officer      Commissioner of Patents and Trademarks